United States Patent [19]

Kelly

[11] Patent Number: 5,681,344
[45] Date of Patent: Oct. 28, 1997

[54] ESOPHAGEAL DILATION BALLOON CATHETER CONTAINING FLEXIBLE NITINOL WIRE

[75] Inventor: Patrick A. Kelly, Kernersville, N.C.

[73] Assignee: Wilson-Cook Medical Inc., Winston-Salem, N.C.

[21] Appl. No.: 384,114

[22] Filed: Feb. 6, 1995

[51] Int. Cl.$^6$ .................................................. A61M 29/00
[52] U.S. Cl. ........................... 606/194; 604/96; 604/281
[58] Field of Search ................................. 604/95, 96, 99, 604/171, 103, 264, 266, 280, 281, 283, 282; 128/772; 606/106, 108, 192, 194

[56] References Cited

U.S. PATENT DOCUMENTS

| | | | |
|---|---|---|---|
| 4,597,755 | 7/1986 | Samson et al. | |
| 4,998,917 | 3/1991 | Gaiser et al. | 604/96 |
| 4,998,923 | 3/1991 | Samson et al. | 606/194 |
| 5,042,985 | 8/1991 | Elliott et al. | 606/192 |
| 5,055,109 | 10/1991 | Gould et al. | 604/95 |
| 5,087,246 | 2/1992 | Smith . | |
| 5,201,754 | 4/1993 | Crittenden et al. | 606/194 |
| 5,232,445 | 8/1993 | Bonzel . | |
| 5,242,394 | 9/1993 | Tremulis . | |
| 5,269,793 | 12/1993 | Simpson . | |
| 5,397,305 | 3/1995 | Kawula et al. | 604/96 |
| 5,456,665 | 10/1995 | Postell et al. | 604/96 |

OTHER PUBLICATIONS

Flexmedics, "Nitinol . . . The Material of Choice for Safer, More Effective Medical Procedures", 1989.

Primary Examiner—Corrine M. McDermott
Assistant Examiner—Cris L. Rodriguez
Attorney, Agent, or Firm—Richard J. Godlewski

[57] ABSTRACT

A kink-resistant catheter, such as a balloon dilation catheter (10) useful in endoscopic or other surgical procedures, includes a flexible nitinol wire (24) having a transition temperature well above the temperature of the body. The catheter (10) remains essentially unkinked through acute bends and turns which would unacceptably kink comparable catheters having wires of stainless steel or other materials. The potential for patient injury from the catheter is thereby reduced. The catheter (10) includes a tubular catheter shaft (12) having a fluid flow lumen (14) defined therein, an expandable but nondistending balloon (18) connected to a distal end (16) of the shaft (12) in fluid communication with the lumen (14), and a flexible catheter tip (22) on the balloon (18) opposite the catheter shaft (12). The nitinol wire (24) preferably extends the entire length of the catheter shaft (12) through the flow lumen (14) and includes a tapered portion (28) extending from a location (30) within the balloon (18) to a distal end (26) of the nitinol wire (24) in the flexible catheter tip (22). The longitudinal positions of the nitinol wire (24) and the balloon (18) relative to one another are fixed by a radiopaque insert (32) in the distal end (16) of the catheter shaft (12), crimped about the nitinol wire (24).

17 Claims, 2 Drawing Sheets

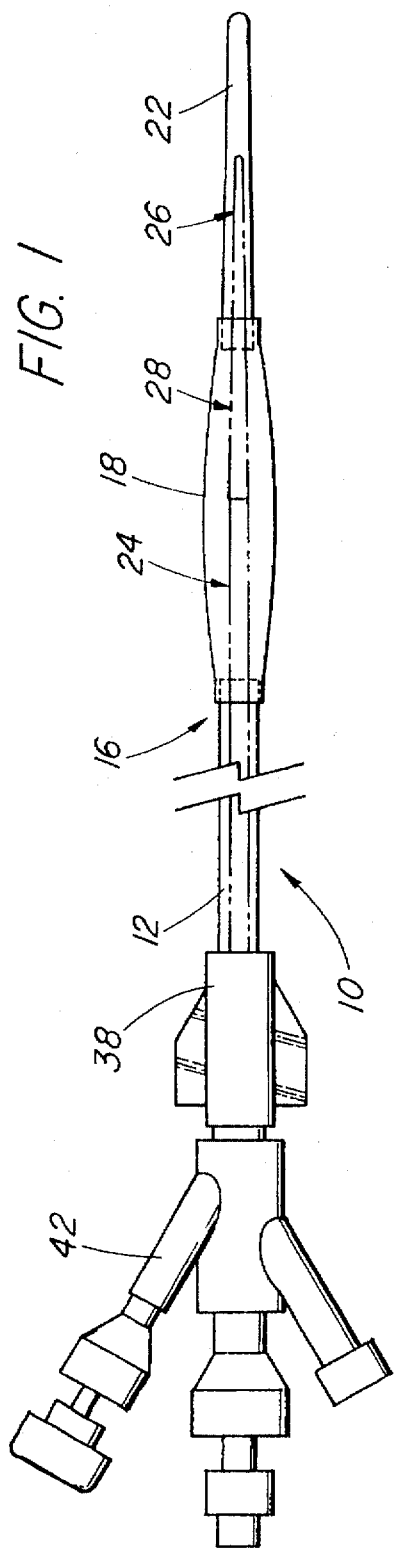
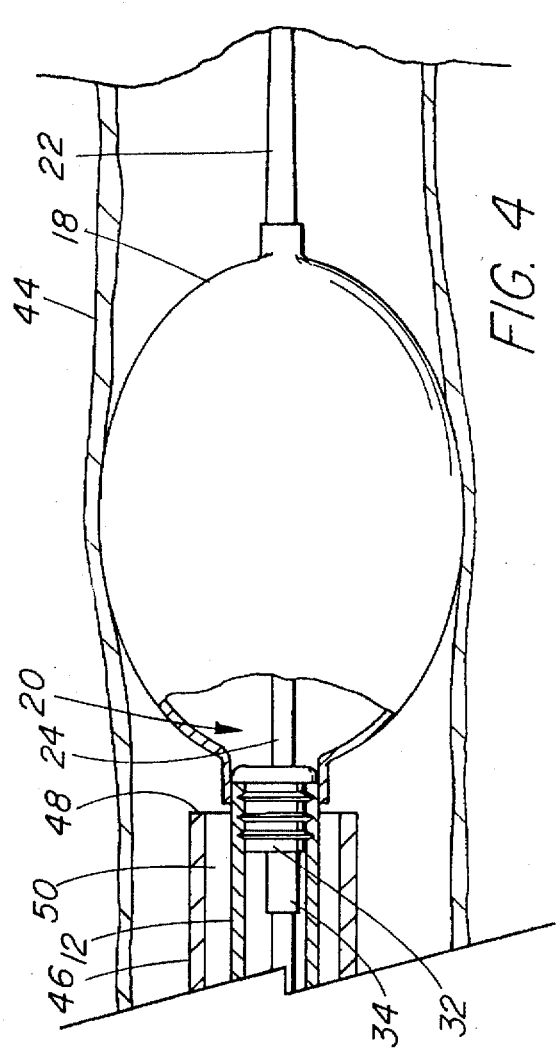
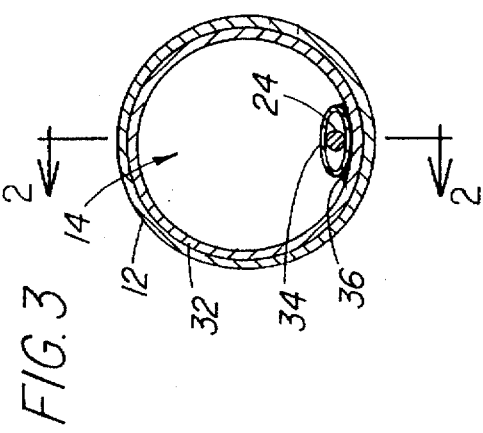

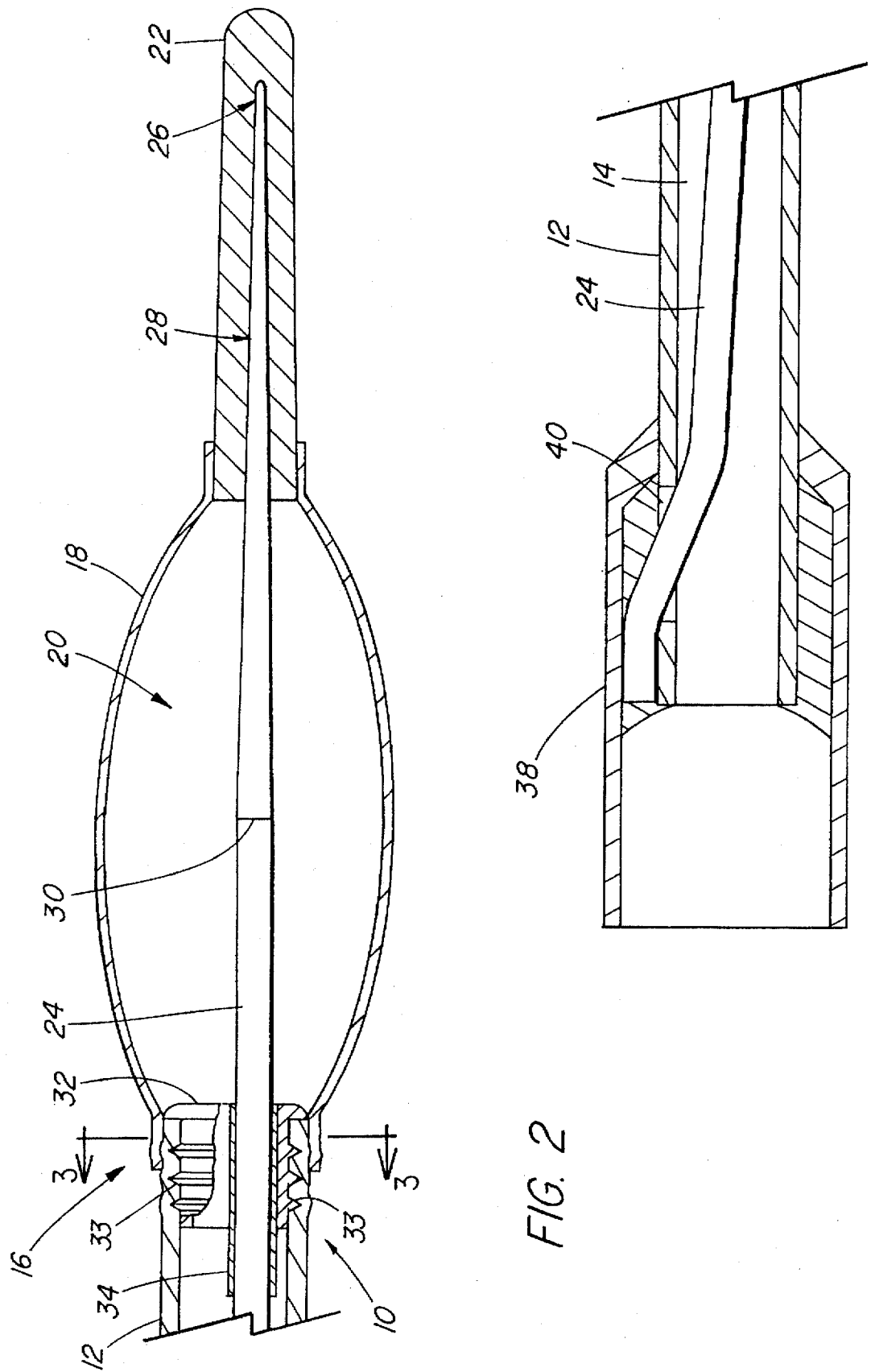

ESOPHAGEAL DILATION BALLOON CATHETER CONTAINING FLEXIBLE NITINOL WIRE

TECHNICAL FIELD

This invention relates generally to surgical devices, and more particularly to catheters, dilators and other devices for establishing, restoring or enlarging lumens in the body, especially in the esophagus.

BACKGROUND OF THE INVENTION

A variety of body lumens are subject to undesired strictures or narrow regions. For example, blood vessels can be blocked or narrowed by atherosclerosis, while esophageal strictures can arise from individual anatomical differences, or from diseases such as connective tissue disorder. Procedures for dilating or enlarging such strictures or narrowed regions often entail the use of a balloon dilation catheter. Such catheters include a deflated balloon which can be positioned across a particular stricture or narrowed region, and which is then inflated with a fluid in order to widen the lumen without trauma to the wall of the lumen.

A variety of balloon catheters and dilators are known which include a balloon attached to the distal end of a catheter tube or shaft, and which also include a stainless steel wire stiffener extending through the catheter shaft and balloon. For example, a balloon dilator as disclosed in U.S. Pat. No. 5,087,246 and sold under the tradename "ELIMINATOR" by C.R. Bard, Inc. (Tewksbury, Mass.) includes a radiopaque polyurethane catheter tube having a stainless steel guide wire internally fixed therein by an insert, and a high pressure, nondistending PET (polyethylene terephthalate) balloon through which the guide wire also passes. The stainless steel wire has a blunt end contained in a plastic tip on the catheter. In use, the catheter is passed through the channel of an endoscope until the balloon fully clears the distal end of the endoscope channel and is positioned across the stricture to be dilated, and a pressurizing liquid is supplied to the balloon through the catheter tube, so as to expand the balloon and dilate the stricture.

A similar balloon catheter is sold under the tradename "MaxForce TTS" and the registered trademark "MICROVASIVE" by Boston Scientific Corporation (Watertown, Mass.). The insert for fixing the stainless steel wire it contains is somewhat longer than the insert of the Bard device, however, and its tapered plastic catheter tip includes a ball on the end. A more significant structural difference lies in the way in which the end of the stainless steel wire stiffener is formed in the plastic tip. In the plastic tip, fully outside and distal to the catheter balloon, a second wire having a reduced and tapering diameter is affixed by wrapping or welding to the stiffener wire.

A significant problem with these types of balloon catheters is that their stainless steel stiffener wires tend to kink or bend during introduction of the catheter into the esophagus. Such kinking undesirably increases the risk that the distal portion of the catheter will unintentionally advance through the lumen wall, and perforate or rupture the esophagus or other tissue defining the lumen. This trauma to the esophagus or other tissue not only requires immediate termination of the specific dilation procedure, it also requires immediate surgical repair and drainage of the traumatized area, to avoid complications such as mediastinitis and pleural effusion.

Tapering of the distal end of the stainless steel stiffener wire, that is, at the catheter tip, is inadequate to solve this problem. It has been found that the tapered portion of the steel wire is even more susceptible to kinking than is the rest of the steel wire, despite encasement of the taper in a flexible plastic catheter tip. As a result, the catheter kinks or bends at its distal end, and thereby retains the potential for injuring the esophagus or other lumen wall during introduction past the distal end of the endoscope channel. Even if the kinks and permanent bends are not so severe as to penetrate the body lumen, they are still undesirable because they restrict movement of the catheter within the endoscope channel, making manipulation of the catheter more difficult and prolonging the dilation procedure.

Other dilators and catheters are known, but they similarly fail to solve this problem, or have their own drawbacks during use. For example, U.S. Pat. No. 4,597,755 (Samson et al., Jul. 1, 1986) discloses a large bore balloon catheter having a coil spring secured to the distal end of a main shaft tube in the region of a balloon, and flexible tubing positioned over the exterior of the coil spring and extending beyond the distal end of the spring. The coil spring aids resistance to kinking. U.S. Pat. No. 5,232,445 (Bonzel, Aug. 3, 1993) discloses a coronary dilation balloon catheter which is slidable along a guidewire extending through a balloon, and which includes a segment of flexible tubing through the balloon for passage of the guidewire. Finally, U.S. Pat. No. 5,269,793 (Simpson, Dec. 14, 1993) discloses a guide system for intravascular catheters which includes both a fixed guide wire extending through and secured to the distal end of a balloon, and a movable guide wire. With respect to the present disclosure, it should be noted that the use of the guide wires in these latter two devices may encounter the same risks of tissue perforation or rupture as may be encountered in the use of the Bard and Boston Scientific devices.

SUMMARY OF THE INVENTION

The foregoing problems are solved and a technical advance is achieved in an illustrative balloon dilation catheter or other catheter. It has been discovered that the undesirable kinking and bending encountered in the use of balloon catheters having stainless steel stiffener wires can be reduced several or even many times, by an elegant yet remarkably simple expedient—using a nitinol wire stiffener in place of the stainless steel stiffener wire. The nitinol wire has a transition temperature well below the temperature of the body and thereby remains superelastic and extremely flexible during the use of the catheter, permitting the catheter to remain essentially unkinked during use. The nitinol wire thereby improves the pushability and trackability of the catheter, that is, it renders the catheter easier to manipulate, in contrast to catheters containing stainless steel wires.

More particularly, balloon and other catheters according to the present invention can be passed through turns of substantially sharper radius without encountering appreciable kinking or permanent bending, in comparison to prior catheters of comparable size employing stainless steel. "Substantially sharper radius" means that the radius of curvature at the bend can be a small fraction, typically one-third to one-tenth, of a radius bend which would appreciably kink a stainless steel-stiffened catheter. The determination of whether a particular degree of kinking or bending is appreciable is a practical one, and is not readily subject to being stated in numerical terms. However, it is believed that those even rudimentarily skilled in this art should readily be able to determine whether a particular kink or permanent bend unacceptably interferes with the utility of a particular catheter or dilator. In the absence of any practical interference, and in the absence of any increase in the risk of tissue perforation or rupture, a particular kink or bend should not be considered appreciable. The important point to note in this regard is that the catheter of the present invention remains usable when subjected to turn radii which would unarguably render stainless steel-stiffened catheters unusable.

In a first aspect, then, the present invention is directed to a flexible and kink-resistant balloon catheter which comprises a catheter shaft having a flow lumen defined therein; a catheter balloon connected to the distal end of the catheter shaft, having an interior in fluid communication with the catheter lumen; a flexible catheter tip on the balloon opposite the catheter shaft; and a flexible nitinol wire positioned in at least the catheter balloon and the flexible tip. Preferably, the nitinol wire extends the entire length of the catheter shaft within the flow lumen, and includes a tapered portion extending from a location within the catheter balloon, to the distal end of the wire. Also preferably, the catheter further comprises a radiopaque insert in the distal end of the catheter shaft which fixes the longitudinal position of the nitinol wire and catheter balloon with respect to one another. The catheter balloon is conveniently nondistending and can be composed of PET or another medical grade material. Also conveniently, the catheter can further include a Luer-lock hub connected to the catheter shaft opposite the distal end of the shaft. This aspect of the invention finds particular utility in esophageal dilators.

In a second aspect, the present invention is directed to a balloon dilation catheter comprising, in combination, the particular parts mentioned above. This aspect of the invention finds particular utility in esophageal dilators as well.

In a final aspect, the present invention is directed to an improvement in catheters of any type, balloon or otherwise, which include a flexible catheter shaft with a flow lumen defined therein, and a flexible catheter tip connected to the catheter shaft; in which the improvement comprises a flexible nitinol wire contained in the catheter shaft and the catheter tip, thereby preventing appreciable kinking of the flexible catheter shaft and catheter tip when inserted into the body. The improvement is preferably embodied in a balloon catheter in which the catheter balloon connects the catheter tip to the catheter shaft. The improvement preferably further comprises the various parts mentioned above. It is important to note, however, that this aspect of the present invention is not limited to balloon or large bore catheters, such as esophageal dilators.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which:

FIG. 1 is a perspective view of the preferred embodiment of the present invention;

FIG. 2 is an enlarged cross-sectional view taken in the plane of FIG. 1 and as taken along line 2—2 of FIG. 3;

FIG. 3 is a cross-sectional view taken along line 3—3 of FIG. 2; and

FIG. 4 is a partial view of the preferred embodiment of the present invention, during endoscopic use.

DETAILED DESCRIPTION

With reference to FIGS. 1 and 2, a flexible and kink-resistant catheter according to the present invention is thereshown, embodied in an esophageal dilation balloon catheter 10. The balloon catheter 10 first comprises a tubular catheter shaft 12 including a flow lumen defined therein, and a distal end 16 adapted for insertion into the body through an endoscopic channel. The catheter shaft 12 is preferably composed of a flexible, medical grade tubing such as polyurethane. The particular dimensions of the catheter shaft 12 are selected as convenient; for esophageal applications, for example, the shaft 12 can be about 200 cm long (but, as explained further below, cut to match the size of the contained nitinol wire), 0.085 inches in outer diameter, and about 0.058 inches in inside diameter.

The catheter 10 also comprises a nondistending catheter balloon 18 connected to the distal end 16 of the catheter shaft 12. The balloon 18 is preferably composed of a physiologically inert, medical grade synthetic, such as PET (polyethylene terephthalate) or the like. The balloon 18 has an interior 20 in fluid communication with the flow lumen 14 in the catheter shaft 12. However, for ease of introduction of the balloon 18 into the body and across the stricture of interest, the balloon 18 is initially maintained in an empty, collapsed state. The balloon 18 overlaps the distal end 16 of the catheter shaft 12 and is connected to and sealed to it by a suitable medical grade adhesive, for example, an ultraviolet curing adhesive. For esophageal applications, it has been found convenient to employ a balloon 18 having length of about 8 cm and a diameter (when expanded from its collapsed state) of about 6 to 18 mm. The process for making the balloon 18 is explained in more detail below.

The catheter 10 next comprises a flexible catheter tip 22 attached to the catheter balloon 18 opposite the catheter shaft 12. The balloon 18 thus connects the catheter tip 22 to the catheter shaft 12. The flexible tip 22 is conveniently composed of a medical grade elastomeric tubing such as Pellethane 2363-80AE, and can be attached to the balloon 18 with the same adhesive as is used to affix the balloon 18 to the catheter shaft 12. Most conveniently, the flexible tip 22 can be formed from tubing composed of the indicated elastomer, and the central bore of the tubing filled with the adhesive during assembly of the catheter 10. The most distal end of the flexible catheter tip 22 is rounded; conveniently, however, an additional round bead (not shown) may be formed on the most distal end of the flexible tip 22, to facilitate introduction of the catheter 10 into the endoscope channel and the body lumen.

The catheter 10 of the present invention further comprises a solid flexible nitinol wire 24 positioned in at least the catheter balloon 18 and the flexible catheter tip 22. Preferably, the nitinol wire 24 is located within the catheter shaft flow lumen 14, and extends the entire length of the catheter shaft 12. The length of the nitinol wire 24 is selected as convenient; for example, for esophageal applications, the wire 24 can be about 195 cm long.

The precise nitinol composition used for the wire 24 is not believed to be critical to the successful practice of the present invention, as long as the nitinol being used possesses a transition temperature well below body temperature, and possesses its conventional superelasticity and flexibility at body temperature.

As more clearly shown in FIG. 2, the nitinol wire 24 includes a distal end 26 contained in the flexible catheter tip 22, and a uniformly tapered portion 28 extending from a location 30 within the catheter balloon interior 20 to the distal wire end 26. Preferably, the diameter of the tapered portion 28 of the nitinol wire 24 decreases by about two-thirds from the location 30 within the balloon interior 20, to the distal wire end 26. For esophageal applications, the tapered portion 28 of the nitinol wire 24 is conveniently about one to three and preferably about 2 inches long, but these limits arise as much from manufacturing concerns as from criteria for utility.

Conveniently, the nitinol wire 24 is uniform throughout its length, except for the tapered portion 28. For esophageal applications, the bulk of the nitinol wire 24 has a diameter of about 0.027 inches, while the diameter of the tapered portion 28 ranges from this same diameter at the location 30 where tapering begins, down to about 0.010 inches at the distal end 26 of the wire 24.

It may be desirable to select a material for the catheter shaft 12 which is radiopaque. This allows the position of the catheter balloon 18 to be established during introduction into the body lumen, for example, the esophagus. However, the same effect may be achieved by positioning an axially perforate, radiopaque insert 32 in the distal end 16 of the catheter shaft 12, and making the shaft 12 of a material which is not radiopaque and which may be less costly than radiopaque materials. The insert 32 preferably simultaneously serves another purpose, specifically, to fix the longitudinal position of the nitinol wire 24 and the catheter balloon 18 with respect to one another.

The insert 32 is conveniently composed of a physiologically inert, radiopaque material such as 303 stainless steel. The insert 32 is conveniently retained in the distal end 16 of the catheter shaft 12 by a plurality of barbs 33 on its outer surface, which embed in the material of the shaft 12. When retained in this manner, the insert 32 can have an outside diameter about the same as the outside diameter of the catheter shaft 12, and an inside diameter slightly smaller than the inside diameter of the shaft 12.

It has been found that it is difficult to affix the nitinol wire 24 directly to the stainless steel insert 32 by conventional methods such as soldering. This problem is solved by using a separate element connected to and between the insert 32 and the wire 24. More particularly, as more clearly shown in FIG. 3, the insert 32 comprises an internally located cannula 34 through which the nitinol wire 24 passes. The cannula 34 is composed of any physiologically inert metal which can be easily affixed to stainless steel in any conventional manner, for example, by soldering with No. 430 solder (4% Ag, 96% Sn). Conveniently, the cannula 34 is composed of a half-inch long piece of 304 stainless steel of size GA-21XX. The wire 24 is secured in the insert 32 by firmly crimping the cannula 34 onto the wire 24. This positively fixes the longitudinal position of the nitinol wire 24 and the catheter balloon 18 with respect to one another, since each is affixed to the catheter shaft 12.

Returning again to FIGS. 1 and 2, the catheter 10 preferably includes a conventional means for engaging the catheter 10 with devices (not shown) for supplying an inflation fluid to, and withdrawing an inflation fluid from, the flow lumen 14 of the catheter 10. Conveniently, this engaging means can be a female luer hub 38 connected to the catheter shaft 12 opposite the distal end 16 of the shaft 12. The luer hub 38 is of any convenient size or style, for example, ANSI/HIMA MD70.1-1983. The hub 38 can be composed of any physiologically inert, medical grade and generally rigid material. In order to ensure that the nitinol wire 24 does not interfere with connection to the luer hub 38, and to further fix the position of the nitinol wire 24, the wire 24 is formed so as to pass through a lateral port 40 formed through the catheter shaft 12, and embedded inside the luer hub 38.

Manufacture of the balloon catheter 10 described above entails several steps, but can be readily understood. It is important that the manufacture be carried out in compliance with good manufacturing practices (GMPs) and that the construction, attachment and sealing of the various parts be monitored carefully, to ensure that the balloon 18 can expand to its desired diameter when inflated under pressure, without leaking or release of the inflating liquid.

The nitinol wire 24 is first prepared by cutting it to the indicated length, grinding the tapered portion 28 to the indicated diameter and length. The wire is then inserted into a length of catheter shaft tubing, the formed portion passed through the port 40, and the tubing and wire 24 positioned in the luer hub 38. Depending upon the materials used, the hub 38 may be and preferably is molded about the tubing and nitinol wire 24.

Next, the cannula 34 is soldered to the balance of the stainless steel insert 32, the catheter tubing cut to the desired length of the catheter shaft 12, the insert 32 placed into the distal end 16 of the catheter shaft 12 so that the nitinol wire 24 passes through the cannula 34, and the cannula 34 firmly crimped on the wire 24. This assembly is now ready for attachment of the catheter balloon 18.

The balloon 18 is then slipped over the distal end 26 of the wire 24 and the flexible tip 22 bonded to the distal end of the balloon 18. The proximal end of the balloon 18 is then bonded to the distal end 16 of the catheter shaft 12, and the flexible tip 22 bonded to the distal end 26 of the wire 24. Again, all of this bonding is conveniently carried out with a UV-curing adhesive or the like. A bit of excess adhesive is left to form a rounded end or ball on the extremity of the flexible tip 22. The balloon 18 is then compressed or folded to facilitate its introduction into the channel of the endoscope. For convenience, between its manufacture and use the balloon 18 may be covered with a polyurethane or other protective sleeve (not shown).

Use of the catheter 10 for enlarging a stricture in the esophagus is straightforward and conventional. Only a general outline of the procedure follows; those skilled in the art will be well aware of such procedures, and the major difference between the use of prior devices and the catheter of the present invention lies in the substantial reduction in kinking that will be encountered.

As generally shown in FIG. 4, an endoscope 46 is first introduced into a body lumen, such as the esophagus 44, and the distal end 48 of the endoscope channel 50 positioned next to the stricture to be dilated. The catheter 10 is inspected to ensure that it is initially undamaged and free of kinks, and to ensure that the catheter balloon 18 is fully deflated. The catheter 10 is attached at the luer hub 38 to a conventional coupling or connector 42, for supplying an inflating fluid to the balloon 18 (through the catheter shaft flow lumen 14), and withdrawing the fluid from the balloon 18 (again, through the lumen 14). Conveniently, the fluid may be either radiopaque or transparent; saline, water or a contrast mixture are all suitable as inflation fluids. A vacuum draw to ensure initial deflation of the balloon 18 may be established through one arm of the coupling 42 to achieve deflation.

The flexible tip 22, the catheter balloon 18 and the distal end 16 of the catheter shaft 12 are then introduced in sequence into the endoscope channel 50, and the catheter shaft 12 manipulated to advance the balloon 18 and flexible tip 22 through the endoscope channel 50 to the stricture. The balloon 18 is advanced until it lies across the stricture. Care must be taken to ensure that the balloon 18 is completely beyond the distal end 48 of the endoscope channel 50 before inflation of the balloon 18 is begun.

The inflating fluid is supplied under pressure through the coupling 42, and thus through the flow lumen 14 of the catheter shaft 12, to the interior 20 of the balloon 18 in order to inflate the balloon 18 and dilate the stricture in the body lumen 44. The catheter balloon 18 is shown in its inflated condition in FIG. 4, where dilation of the body lumen 44 has been achieved.

Removal of the catheter 10 from the body lumen 44 is essentially a reversal of the introduction scheme. First, the catheter balloon 18 must be fully deflated, and all fluid possible drawn from it. Care must be taken to ensure that the balloon 18 is not withdrawn back into the endoscope channel 50 until the balloon 18 is fully deflated. The proximal end of the catheter 10 is grasped, and the catheter 10 carefully withdrawn from the endoscope channel.

It is thus clear that the present invention provides a simple yet extremely kink-resistant balloon dilation catheter or other catheter which is useful in endoscopic or other surgical procedures. This resistance to kinking is achieved by the use of a nitinol wire extending through at least the catheter balloon and catheter tip, and preferably extending through the entire length of the catheter lumen.

Industrial Applicability

The present invention is useful in the performance of surgical procedures, and therefore finds applicability in human and veterinary medicine.

It is to be understood, however, that the above-described dilator, catheter or the like is merely an illustrative embodiment of the principles of this invention, and that other dilators, catheters or the like, and methods for using them, may be devised by those skilled in the art, without departing from the spirit and scope of the invention. It is also to be understood that the invention encompasses embodiments both comprising and consisting of the disclosed parts. Accordingly, it is clear that the nitinol wire 24 solely and by itself provides the catheter of the present invention with a uniform and continuous resistance to transverse deflection distal to the location 30 within the catheter balloon interior 20.

What is claimed is:

1. A flexible and kink-resistant balloon catheter, comprising:

a catheter shaft (12) including a flow lumen (14) defined therein, the catheter shaft (12) having a distal end (16);

a catheter balloon (18) connected to the distal end (16) of the catheter shaft (12), having an interior (20) in fluid communication with the flow lumen (14) of the catheter shaft (12), and further having a location (30) defined within the interior (20) of the catheter balloon (18);

a flexible catheter tip (22) on the catheter balloon (18) opposite the catheter shaft (12); and means providing the catheter with resistance to transverse deflection and preventing appreciable kinking of the catheter distal to the location (30), consisting of a flexible nitinol wire (24) positioned in at least the catheter balloon (18) and the flexible tip (22) on the catheter balloon (18);

wherein the nitinol wire (24) includes a distal end (26) contained in the flexible catheter tip (22) and a uniformly tapered portion (28) extending from the location (30) within the catheter balloon interior (20) to the distal wire end (26).

2. The catheter according to claim 1, wherein the tapered portion (28) of the nitinol wire (24) has a diameter which decreases by about two-thirds from the location (30) within the interior (20) of the catheter balloon (18) to the distal wire end (26).

3. The catheter according to claim 1, wherein the tapered wire portion (28) is about one to three inches long.

4. The catheter according to claim 1, further comprising a radiopaque insert (32) in the catheter shaft distal end (16), fixing the longitudinal position of the nitinol wire (24) and the catheter balloon (18) with respect to one another.

5. The catheter according to claim 4, wherein the insert (32) comprises a cannula (34) crimped about the nitinol wire (24).

6. The catheter according to claim 1, wherein the catheter balloon (18) is composed of PET.

7. The catheter according to claim 1, wherein the nitinol wire (24) is solid and extends the entire length of the catheter shaft (12) within the catheter shaft flow lumen (14).

8. The catheter according to claim 1, further comprising a luer hub (38) connected to the catheter shaft (12) opposite the catheter shaft distal end (16).

9. A flexible and kink-resistant balloon catheter, comprising:

a catheter shaft (12) including a flow lumen (14) defined therein, the catheter shaft (12) having a distal end (16);

a luer hub (38) connected to the catheter shaft (12) opposite the catheter shaft distal end (16);

a PET catheter balloon (18) connected to the distal end (16) of the catheter shaft (12), having an interior in fluid communication with the flow lumen (14) of the catheter shaft (12), and further having a location (30) defined within the interior (20) of the catheter balloon (18);

a flexible catheter tip (22) on the catheter balloon (18) opposite the catheter shaft (12);

a flexible nitinol wire (24) positioned in the catheter shaft flow lumen (14) and in the catheter balloon interior (20), the nitinol wire (24) extending the entire length of the catheter shaft (12) and having a distal end (26) positioned in the flexible catheter tip (22) on the catheter balloon (18), and the nitinol wire (24) further including a tapered portion (28) about one to three inches long extending from the location (30) within the interior (20) of the catheter balloon (18) to the distal wire end (26); and a radiopaque insert (32) in the catheter shaft distal end (16) fixing the longitudinal position of the nitinol wire (24) and the catheter balloon (18) with respect to one another, the insert (32) comprising a cannula (34) crimped about the nitinol wire (24).

10. In a catheter adapted for insertion into the body (44), the catheter including a flexible catheter shaft (12) with a flow lumen (14) defined therein, a flexible catheter tip (22) connected to the catheter shaft (12) and a catheter balloon (18) positioned between and connecting the catheter shaft (12) and the flexible catheter tip (22), the catheter balloon (18) having an interior in fluid communication with the flow lumen (14) of the catheter shaft (12), and further having a location (30) defined within the interior (20) of the catheter balloon (18); the improvement comprising means providing the catheter with resistance to transverse deflection and preventing appreciable kinking of the catheter distal to the location (30), consisting of a flexible nitinol wire (24) contained in the catheter shaft (12) and the catheter tip (22), wherein the nitinol wire (24) includes a distal end (26) contained in the flexible catheter tip (22) and a uniformly tapered portion (28) extending from the location (30) within the interior (20) of the catheter balloon (18) to the distal wire end (26).

11. The improvement according to claim 10, wherein the tapered portion (28) of the nitinol wire (24) has a diameter which decreases by about two-thirds from the location (30) within the interior (20) of the catheter balloon (18) to the distal wire end (26).

12. The improvement according to claim 10, wherein the tapered wire portion (28) is about one to three inches long.

13. The improvement according to claim 10, wherein the catheter shaft (12) has a distal end (16), and wherein the improvement further comprises a radiopaque insert (32) in the catheter shaft distal end (16), fixing the position of the nitinol wire (24) and the catheter balloon (18) with respect to one another.

14. The improvement according to claim 13, wherein the insert (32) comprises a cannula (34) crimped about the nitinol wire (24).

15. The improvement according to claim 10, wherein the catheter balloon (18) is composed of PET.

16. The improvement according to claim 10, wherein the nitinol wire (24) is solid and extends the entire length of the catheter shaft (12) within the catheter shaft flow lumen (14).

17. The improvement according to claim 10, wherein the catheter further comprises a luer hub (38) connected to the catheter shaft (12) opposite the catheter shaft distal end (16), and wherein the nitinol wire (24) is connected to the luer hub (38).

* * * * *